(12) United States Patent
Binz et al.

(10) Patent No.: US 6,950,762 B2
(45) Date of Patent: Sep. 27, 2005

(54) DEVICE FOR EXAMINING LIQUIDS

(75) Inventors: Dieter Binz, Hirshberg (DE); Albrecht Vogel, Stutensee (DE)

(73) Assignee: ABB Research Ltd., Zurich (CH)

( * ) Notice: Subject to any disclaimer, the term of this patent is extended or adjusted under 35 U.S.C. 154(b) by 0 days.

(21) Appl. No.: 10/668,084

(22) Filed: Sep. 22, 2003

(65) Prior Publication Data

US 2004/0098211 A1 May 20, 2004

(30) Foreign Application Priority Data

Mar. 20, 2001 (DE) .......................... 101 13 646

(51) Int. Cl.$^7$ ............................................ G06F 19/00
(52) U.S. Cl. ....................................................... 702/50
(58) Field of Search ............................ 702/50; 134/18; 435/13; 455/418, 559; 713/153; 320/338; 333/26; 759/206; 370/352; 711/103; 347/104; 323/222; 607/60; 600/300, 561; 604/66; 204/411, 435, 403; 250/239

(56) References Cited

U.S. PATENT DOCUMENTS 5,260,872 A  11/1993 Copeland et al. ............. 435/13
6,123,820 A   9/2000 Bergkuist et al.
6,193,864 B1  2/2001 Leader et al.
6,628,208 B1 * 9/2003 Morozumi et al. .... 340/870.28
2002/0082665 A1 * 6/2002 Haller et al. .................. 607/60

FOREIGN PATENT DOCUMENTS

| FR | 2 417 774 | 9/1979 |
| JP | 61122555 | 6/1986 |
| WO | 2 069 702 A | 8/1981 |
| WO | 94/19684 | 9/1994 |

* cited by examiner

Primary Examiner—Bryan Bui
Assistant Examiner—Tung S. Lau
(74) Attorney, Agent, or Firm—Laurence A. Greenberg; Werner H. Stemer; Ralph E. Locher

(57) ABSTRACT

A device for examining liquids. A precise examination of liquids has until now only been possible where there are permanently installed evaluation devices. This disadvantage can be avoided with the device for testing liquids. It is equipped with a sensor, which has a measuring device with which any liquid can be examined. The sensor is able to be electrically and mechanically connected to a structural unit which is only slightly larger than a mobile radio telephone. Integrated into the structural unit are an evaluation device and an interface module. The measuring signals of the sensor are registered by the interface module and stored, evaluated and displayed on a display device in the evaluation device.

5 Claims, 1 Drawing Sheet

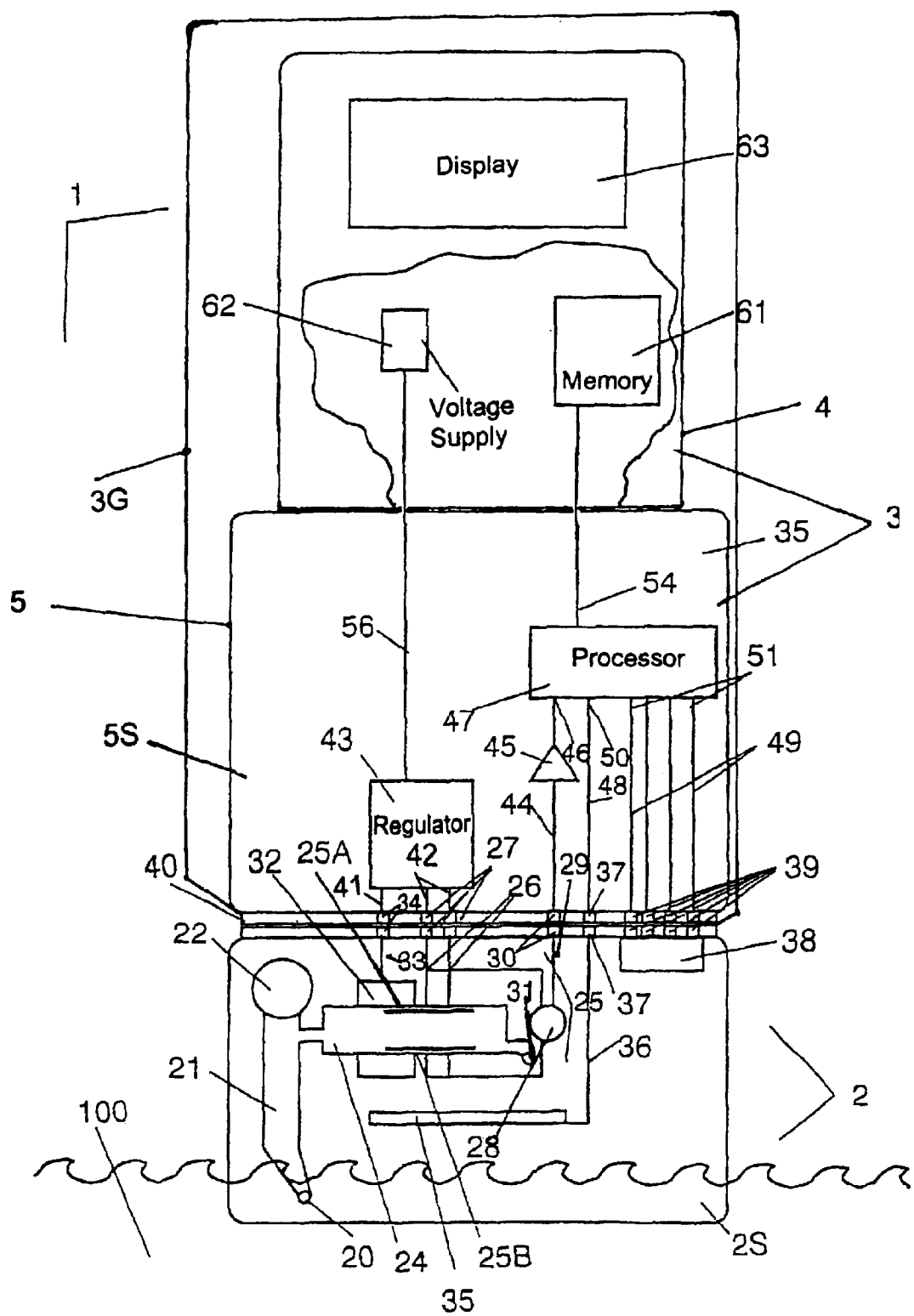

DEVICE FOR EXAMINING LIQUIDS

CROSS-REFERENCE TO RELATED APPLICATION

This application is a continuation of copending International Application No. PCT/EP02/02986, filed Mar. 19, 2002, which designated the United States and was not published in English.

BACKGROUND OF THE INVENTION

Field of the Invention

The invention relates to a device for examining liquids that has at least one exchangeable sensor connected to an evaluation device through an interface module.

Such a device is used for example for the monitoring of liquids in sewage plants.

For inspecting liquids, until now calorimetric test devices have for example been used. They contain a test cell, a mixture of chemical reagents in solid or liquid form, weighed out precisely and of a composition optimally selected for the measuring task, and an evaluation and display unit. For carrying out the test, a small amount of the liquids to be examined is filled into the cell, mixed with the reagents, shaken up or, if appropriate, additionally heated. This produces a color reaction, the intensity of which is characteristic of the components to be demonstrated in the liquid. The color intensity is determined by the evaluation and display unit and converted into a concentration of the substance sought. A disadvantage of this type of liquid examination is the relatively complicated procedure for the measurement, which requires knowledge of laboratory techniques on the part of the user, and also the high price of the evaluation and display unit.

Furthermore, paper-based or plastic-based test strips are known. These have applied to one end of them chemical reagents that are adjusted to the paper and specific for the substance to be detected. The test strips are dipped into the liquid to be examined. If the substance sought is contained in the liquid in a concentration that is not negligible, it produces with the reagents on the paper a color reaction, the intensity of which is a measure of the concentration in the liquid of the substance sought. No sample has to be taken, the test strip can be dipped directly into the liquid to be examined. A known example of this type of liquid examination is that of pH test sticks. A disadvantage of the test sticks is that only simple ion-selective reactions can be realized. Biological parameters such as the biological oxygen demand or more complex chemical parameters such as the chemical oxygen demand of a liquid cannot be determined with them.

Furthermore, small compact analysis systems with a volume of approximately 50 cm$^3$ are known. The liquid to be examined is introduced by a pipette. The analysis system is then disposed in a separate external evaluation and display unit. This unit contains devices in the form of mechanical and/or electroosomotic pumps, with the aid of which the liquid samples can be moved through channels in the analysis system. The unit also provides the auxiliary energy for the detection of the component sought. In the evaluation, electrochemical and/or optical detection methods are carried out. Considerable auxiliary energy is required for this purpose. The disadvantage of this type of liquid examination is that an expensive and complicated external evaluation and display unit is required.

SUMMARY OF THE INVENTION

It is accordingly an object of the invention to provide a device for examining liquids that overcomes the above-mentioned disadvantages of the prior art devices of this general type, which inspects liquids very precisely, in a simple and low-cost way.

With the foregoing and other objects in view there is provided, in accordance with the invention, an apparatus for examining liquids. The apparatus contains a structural device, and an evaluation device integrated in the structural device. The evaluation device has a data memory, a voltage supply unit, a display device, an operating system, a processor, and components for a mobile radio function. An interface module is integrated in the structural device. The interface module has at least one voltage regulator, a preamplifier and a processor. At least one exchangeable sensor is connected to the evaluation device through the interface module. The exchangeable sensor is formed as a card and has at least one measuring device, a sample receiving channel, a heating element, a temperature sensor and a coding device. The exchangeable sensor is electrically and mechanically connected to the structural unit in an inserted state. Serial electrical plug-in connections are disposed on the interface module and the exchangeable sensor for connecting the interface module to the exchangeable sensor.

In accordance with an added feature of the invention, an electrical conductor track connects the voltage regulator to the voltage supply unit, and a serial data line connects the processor of the interface module to the data memory of the evaluation device.

In accordance with a further feature of the invention, signal lines are provided and the preamplifier has a signal output. The processor of the interface module has signal inputs connected to the signal output of the preamplifier. The signal inputs are further connected to the temperature sensor and the coding device through the signal lines and the serial electrical plug-in connections.

In accordance with another feature of the invention, the measuring device has electrodes and a signal output and the preamplifier has an input. The exchangeable sensor has a signal line connected between the signal output of the measuring device and one of the series electrical plug-in connections. The signal output is connected to the input of the preamplifier through the signal line and one series electrical plug-in connection. The exchangeable sensor has electrical conductor tracks connected between the heating element and the serial electrical plug-in connections and between the electrodes and the serial electrical plug-in connections. The heating element and the electrodes are connected to the voltage regulator through the electrical conductor tracks and the serial electrical plug-in connections.

In accordance with an additional feature of the invention, the coding device contains details concerning a measuring range, measuring parameters, a number of measurements which can still be performed and have already been carried out, a batch number, a date of manufacture and a service life of the exchangeable sensor.

Other features which are considered as characteristic for the invention are set forth in the appended claims.

Although the invention is illustrated and described herein as embodied in a device for examining liquids, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE DRAWINGS

The single FIGURE of the drawing is an illustration of a device for testing liquids.

DESCRIPTION OF THE PREFERRED EMBODIMENTS

Referring now to the single figure of the drawing in detail, there is shown a device 1, which has a sensor 2 and a structural unit 3. The structural unit 3 is bounded outwardly by a housing 3G, into which an evaluation device 4 and an interface module 5 are integrated. The sensor 2 is formed as a flat type of component and is produced from plastic, ceramic or silicon. The thickness of the sensor 2 is approximately five millimeters. Its surface 2S has in the case of the exemplary embodiment represented here a size of 5×8 cm². If need be, however, its dimensions may also be chosen differently. The sensor 2 is provided with an inlet opening 20. Via the inlet opening 20, a defined amount of liquid 100 can be introduced into a sample receiving channel 21, which directly adjoins the inlet opening 20. Integrated into the sample receiving channel 21 is a mechanical pump 22. It is formed by a recess in the surface 2S and a non-illustrated film stretched over the latter. Branching off from the sample receiving channel 21 is a measuring channel 24, which belongs to a measuring device 25. The latter has two electrodes 25A and 25B, which are disposed inside the measuring channel 24. Each of the two electrodes 25A and 25B is connected to an electrical conductor track 26. Each free end of each conductor track 26 is provided with a plug-in connection 27. Connected in parallel with the electrodes 25A and 25B is a current measuring unit 28. Connected to its signal output is a signal line 29, the free end of which is likewise connected to a plug-in connection 30. The measuring channel 24 is provided at its second end with an outlet opening 31, from which the liquid 100 can leave again. In order that the measuring channel 24 and the liquid 100 located in it can be kept at a predeterminable temperature, integrated into the sensor 2 is a heating element 32, which is connected to an electrical supply line 33, the free end of which is provided with a plug-in connection 34. A temperature sensor 35 is also provided. Its signal output is connected to a signal line 36, the free end of which is likewise provided with a plug-in connection 37. Also provided is a coding device 38, the signal outputs of which likewise have plug-in connections 39. The surface 2S of the sensor 2 is provided with non-illustrated recesses, into which the current measuring unit 28, the heating element 32, the temperature sensor 35, the coding device 38 and the electrical conductor tracks 26, 29, 33 and 36 are embedded. The sample receiving channel 21, the pump 22 and the measuring channel 24 are likewise formed by non-illustrated recesses. Provided for outwardly bounding the sensor 2 is a non-illustrated film that stretches over the surface 2S and is firmly connected to the edges of the latter. Only the inlet opening 20 and the outlet opening 31 as well as the plug-in connections 27, 30, 34, 37 and 39 remain freely accessible. The plug-in connections 27, 30, 34, 37 and 39 of the sensor 2 and of the interface module 5 are disposed mirror-symmetrically in relation to one another. The sensor 2 can be connected to the evaluation device 4 via the interface module 5. If circumstances so require, the sensor 2 and the interface module 5 may however also form a structural unit. Since, however, the sensor 2 is discarded after being used once, the structural unit 3 is the less costly variant. The plug-in connections 27, 30, 34, 37 and 39 of the sensor 2 may be electrically and mechanically connected to the plug-in connections 27, 30, 34, 37 and 39 of the interface module 5, in that they are inserted into a slide-in module 40 at the first end of the housing 3G, inside which the plug-in connections 27, 30, 34, 37 and 39 of the interface module 5 are disposed.

The interface module 5 is formed as a flat type of component, which in the case of the exemplary embodiment represented here is produced from plastic. It is equipped with a voltage regulator 43, a preamplifier 45 and a processor 47. The voltage regulator 43, the preamplifier 45 and the processor 47 are embedded in non-illustrated recesses, which are formed in a surface 5S of the interface module 5. The same also applies to the conductor tracks 44 to 56. These may, however, also be routed on the surface 5S. The surface 5S of the interface module 5 is completely closed outwardly by a non-illustrated cover plate, which is likewise produced from plastic. The plug-in connections 27 and 34 are in connection with the voltage regulator 43 via electrical conductor tracks 41 and 42. The plug-in connection 30 is connected via the electrical conductor track 44 to the preamplifier 45, the output of which is connected to a first signal input 46 of the processor 47. The plug-in connections 37 and 39 are connected via electrical conductor tracks 48 and 49 to signal inputs 50 and 51 of the processor 47. Consequently, the heating element 32 and the electrodes 25A and 25B of the measuring device 25 can be connected to the voltage regulator 43 of the interface module 5, while the current measuring unit 28, the temperature sensor 35 and the coding device 38 can be connected to the processor 47, via the plug-in connections 27, 30, 34, 37 and 39. The current measuring unit 28 integrated into the sensor 2 may also be disposed inside the interface module 5, to be precise between the plug-in connection 29 and the signal input of the preamplifier. This may be advisable if the sensor 2 is used only for one measurement and is then discarded.

A computer of dimensions which correspond approximately to those of a mobile radio telephone, and which moreover may have a mobile radio function, is used as the evaluation device 4. For example, a palm computer that is equipped with a mobile radio function may be used as the evaluation device 4. However, any other evaluation device 4 that has these functions and is provided moreover with correspondingly small dimensions may also be used. The evaluation device 4 represented here is provided with a data memory 61, a voltage supply unit 62 and a display device 63. Furthermore, it has an operating system, a processor and also components for a mobile radio. The voltage regulator 43 of the interface module 5 is connected via an electrical conductor track 56 to the voltage supply unit 62, while the processor 47 of the interface module 5 is connected via a serial signal line 54 to the data memory 61 of the evaluation unit 4.

The operating principle of the device 1 according to the invention is explained below. If the biological oxygen demand of the liquid 100, that is located for example in a tank of a non-illustrated sewage plant, is to be determined with the sensor 2, the sensor 2 is electrically and mechanically connected to the structural unit 3 via the plug-in connections 27, 30, 34, 37, and 39. The sensor 2 is then dipped into the liquid 100 to such an extent that the inlet opening 20 is disposed in it. By pressing with a finger, the pump 22 is actuated and the sample receiving channel 21 is emptied. After letting go of the pump, the liquid 100 is sucked into the sample receiving channel 21 and then flows into the measuring channel 24. An electrical voltage is applied to the electrodes 25A and 25B of the measuring device 25. The size of the voltage can be set with the voltage regulator 43 of the interface module 5. The reaction of the liquid 100 with enzymes, bacteria or other reactants that are located in the measuring channel 24 causes organic molecules that are located in the liquid 100 to be split into smaller molecules. The applied voltage brings about an oxidation of these split molecules. The oxides formed have the effect that a current flows between the electrodes 25A and 25B, the size of which is registered by the current measuring unit 28. The size of the current is directly proportional to the amount of the oxides contained in the measuring channel 24. The measuring signal of the measuring device 25 is fed via the preamplifier 45 to the processor 47 of the interface module 5, and is passed on from there to the data memory 61 of the evaluation device 4 for storing of the data. The measured values can be evaluated in the evaluation device 4 and displayed on the display device 63. Moreover, they can also be transmitted to a remote, permanently installed evaluation station. Information concerning the sensor 2 can be inquired on the coding device 38. This information contains details concerning the measuring range, the measuring parameters, the number of measurements which can still be performed or have already been carried out, the batch number, the date of manufacture and the service life of the sensor 2.

We claim:

1. A device for examining liquids, comprising:

a structural device;

an evaluation device integrated in said structural device, said evaluation device having a data memory, a voltage supply unit, a display device, an operating system, a processor, and components for a mobile radio function;

an interface module integrated in said structural device, said interface module having at least one voltage regulator, a preamplifier and a processor;

at least one exchangeable sensor connected to said evaluation device through said interface module, said exchangeable sensor formed as a card and having at least one measuring device, a sample receiving channel for channeling a liquid under test, a heating element for heating the liquid under test, a temperature sensor and a coding device, said exchangeable sensor electrically and mechanically connected to said structural unit in an inserted state; and serial electrical plug-in connections disposed on said interface module and said exchangeable sensor for connecting said interface module to said exchangeable sensor.

2. The device according to claim 1, further comprising:

an electrical conductor track connecting said voltage regulator to said voltage supply unit; and a serial data line connecting said processor of said interface module to said data memory of said evaluation device.

3. The device according to claim 1, further comprising signal lines;

wherein said preamplifier has a signal output; and wherein said processor of said interface module has signal inputs connected to said signal output of said preamplifier, said signal inputs further connected to said temperature sensor and said coding device through said signal lines and said serial electrical plug-in connections.

4. The device according to claim 1, wherein:

said measuring device has electrodes and a signal output;

said preamplifier has an input;

said exchangeable sensor has a signal line connected between said signal output of said measuring device and one of said series electrical plug-in connections, said signal output connected to said input of said preamplifier through said signal line and said one of said series electrical plug-in connections; and said exchangeable sensor has electrical conductor tracks connected between said heating element and said serial electrical plug-in connections and between said electrodes and said serial electrical plug-in connections, said heating element and said electrodes connected to said voltage regulator through said electrical conductor tracks and said serial electrical plug-in connections.

5. The device according to claim 1, wherein said coding device contains details concerning a measuring range, measuring parameters, a number of measurements which can still be performed and have already been carried out, a batch number, a date of manufacture and a service life of said exchangeable sensor.

* * * * *

UNITED STATES PATENT AND TRADEMARK OFFICE
CERTIFICATE OF CORRECTION

PATENT NO.   : 6,950,762 B2
DATED        : September 27, 2005
INVENTOR(S)  : Binz et al.

It is certified that error appears in the above-identified patent and that said Letters Patent is hereby corrected as shown below:

<u>Title page,</u>
Item [63], Related U.S. Application Data, should read as follows:
-- Continuation of application No. PCT/EP02/02986, filed on Mar. 19, 2002 --.

Signed and Sealed this

Twenty-ninth Day of November, 2005

JON W. DUDAS
*Director of the United States Patent and Trademark Office*